(12) United States Patent
Hood, Jr.

(10) Patent No.: US 7,018,337 B2
(45) Date of Patent: Mar. 28, 2006

(54) METHOD AND APPARATUS FOR AUTOMATIC NON-INVASIVE BLOOD PRESSURE MONITORING

(75) Inventor: Rush W. Hood, Jr., Tampa, FL (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 169 days.

(21) Appl. No.: 10/065,698

(22) Filed: Nov. 11, 2002

(65) Prior Publication Data

US 2004/0092831 A1 May 13, 2004

(51) Int. Cl.
*A61B 5/02* (2006.01)

(52) U.S. Cl. .................. 600/490; 600/494; 600/498
(58) Field of Classification Search ................ 600/481, 600/490, 492–499, 500–503; 251/297
See application file for complete search history.

(56) References Cited

U.S. PATENT DOCUMENTS

| 4,112,929 | A | * | 9/1978 | Affeldt et al. ............... 600/493 |
| 4,198,031 | A | * | 4/1980 | Ezekiel et al. ............... 251/117 |
| 4,200,259 | A | * | 4/1980 | Ueda ........................... 251/285 |
| 4,243,201 | A | * | 1/1981 | Speidel ........................ 251/297 |
| 4,262,674 | A | * | 4/1981 | Uemura et al. .............. 600/493 |
| 4,501,280 | A | * | 2/1985 | Hood, Jr. .................... 600/490 |
| 4,566,463 | A | * | 1/1986 | Taniguchi et al. .......... 600/495 |
| 4,690,171 | A | * | 9/1987 | Johnston ..................... 137/877 |
| 4,768,518 | A | | 9/1988 | Peltonen ..................... 128/677 |
| 4,922,918 | A | | 5/1990 | Ruiter ......................... 128/681 |
| 5,054,494 | A | * | 10/1991 | Lazzaro et al. ............. 600/490 |
| 5,464,019 | A | * | 11/1995 | Anderson et al. ........... 600/490 |

* cited by examiner

*Primary Examiner*—Robert L. Nasser
*Assistant Examiner*—Navin Natnithithadha
(74) *Attorney, Agent, or Firm*—Cantor Colburn LLP

(57) ABSTRACT

An automatic non-invasive blood pressure monitoring system includes a blood pressure monitor, a blood pressure cuff pneumatically connected to the blood pressure monitor, a deflation valve connected intermediate the blood pressure monitor and the blood pressure cuff, and a controller for automatically controlling the non-invasive blood pressure monitoring.

11 Claims, 2 Drawing Sheets

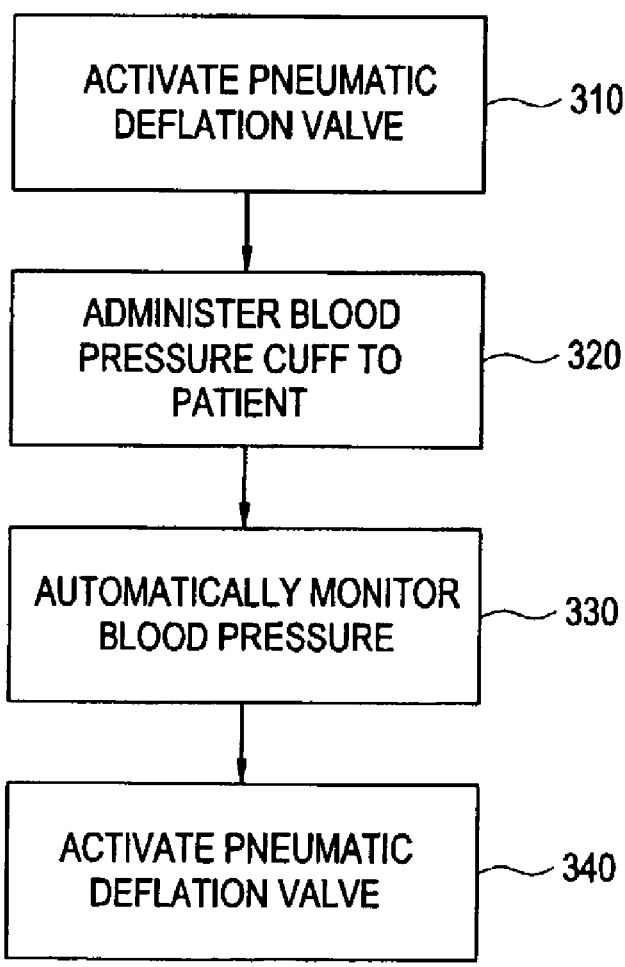

METHOD AND APPARATUS FOR AUTOMATIC NON-INVASIVE BLOOD PRESSURE MONITORING

BACKGROUND OF THE INVENTION

This invention relates generally to blood pressure monitoring, and more particularly to a method and apparatus for automatic non-invasive blood pressure monitoring.

Blood pressure may be measured non-invasively using a cuff applied to an upper or lower extremity, such as the upper arm, for example, that is inflated and deflated to yield a numeric display of systolic, diastolic and mean blood pressure. The method applied using a cuff is referred to as the oscillometric method, since oscillations in the arterial walls created by cardiac contractions are detected. Different cuff sizes are used to accommodate patients of different sizes. If the cuff size is too small for the patient size, it will cause the non-invasive blood pressure (NIBP) monitor to read falsely high. Conversely, too large a cuff can lead to falsely low readings. Thus, a given monitor must be capable of accepting cuffs of different sizes, which are designed so that they can be detached from the monitor. To properly apply the oscillometric method using a cuff, the air within the cuff must be expelled before taking a measurement, since residual air can lead to inaccurate readings caused by a loose-fitting cuff. Additionally, the hose connections between the cuff and the monitor must be checked for air leakage, which can also lead to inaccurate readings.

Present NIBP monitoring systems include both manual and automatic systems. Manual systems typically have manual inflation bulbs and manual deflation valves, which may be found on mercury and aneroid sphygmomanometers, for example, while automatic systems typically have microprocessor controlled cuff inflation systems and electronic read-out units. Some automatic systems also include automatic cuff deflation systems, which are typically controlled by an electronic valve within the monitor. Electronic deflation valves are more costly than manual deflation valves, and large-orifice electronic deflation valves are substantially more costly. To keep the cost of the automatic NIBP monitor at an acceptable level, small-orifice electronic deflation valves, or no deflation valves, are employed. Where a small-orifice electronic deflation valve or no deflation valve is used, a user may resort to manual squeezing of the cuff, or complete detachment of the cuff hose from the monitor, in order to quickly deflate the cuff, which may add wear and tear to the cuff and hose and is typically considered an inconvenience to the user.

BRIEF DESCRIPTION OF THE INVENTION

In one embodiment, an automatic non-invasive blood pressure monitoring system includes a blood pressure monitor, a blood pressure cuff pneumatically connected to the blood pressure monitor, a deflation valve connected intermediate the blood pressure monitor and the blood pressure cuff, and a controller for automatically controlling the non-invasive blood pressure monitoring.

In another embodiment, a method for automatic non-invasive blood pressure monitoring of a patient includes actuating a deflation valve to deflate a blood pressure cuff prior to administering the blood pressure cuff to a patient, automatically monitoring the blood pressure of the patient using the blood pressure cuff and an automatic blood pressure monitor, and actuating the deflation valve to deflate the blood pressure cuff for removal of the blood pressure cuff from the patient after completion of the blood pressure monitoring.

In a further embodiment, a deflation valve for an automatic non-invasive blood pressure monitoring system includes a valve body, a monitor port at a first end of the valve body for receiving a monitor hose, a cuff port at a second end of the valve body for receiving a cuff hose, and an air channel intermediate the monitor and cuff ports. The air channel has a sealable exhaust port for exhausting air from the air channel to ambient.

BRIEF DESCRIPTION OF THE DRAWINGS

Referring now to the figures, which are exemplary embodiments, and wherein like elements are numbered alike:

FIG. 3 depicts a process flowchart for automatic non-invasive blood pressure monitoring in accordance with an embodiment of the invention.

DETAILED DESCRIPTION OF THE INVENTION

Figure 1:
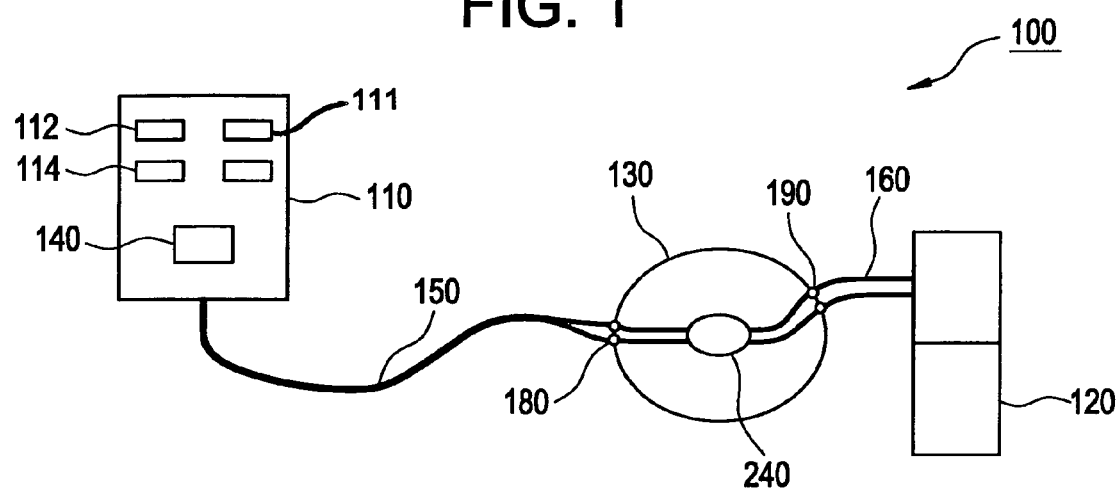
FIG. 1 depicts a schematic representation of an automatic non-invasive blood pressure monitoring system in accordance with an embodiment of the invention.
Figure 2:
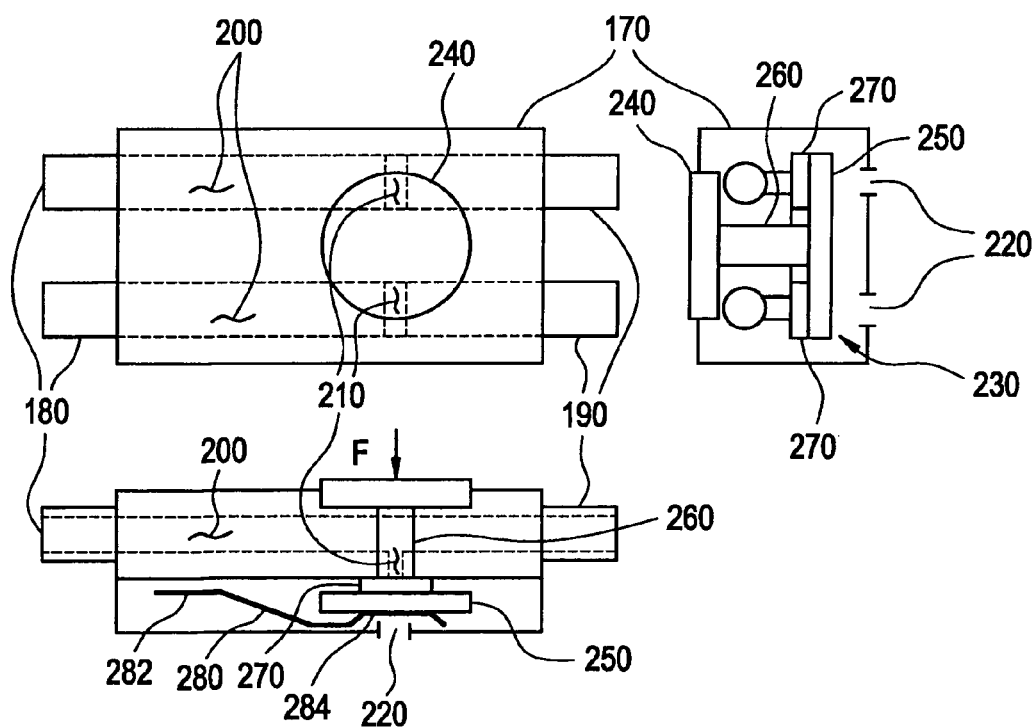
FIG. 2 depicts an orthogonal view of a non-invasive blood pressure deflation valve as used in the system of FIG. 1.

A detailed description of an embodiment of the present invention is presented herein by way of exemplification and not limitation with reference to FIGS. 1–3.

Referring to FIG. 1, an automatic non-invasive blood pressure (NIBP) monitoring system 100 is shown to include a blood pressure monitor 110, which is typically an automatic NIBP monitor as discussed below, a blood pressure cuff 120 pneumatically connected to blood pressure monitor 110, a pneumatic deflation valve 130 connected intermediate blood pressure monitor 110 and blood pressure cuff 120, and a controller 140, which is typically, but not necessarily, arranged within blood pressure monitor 110. If controller 140 is arranged external to blood pressure monitor 110, it may be incorporated into a personal computer (not shown) that is in electrical communication with blood pressure monitor 110. Controller 140 implements logic for automatically controlling the NIBP monitoring process. Blood pressure monitor 110 typically also includes a display 112 for displaying blood pressure information, and controls 114 for providing an interface between a user and controller 140. In an embodiment, pneumatic deflation valve 130 is a manually operated pneumatic deflation valve, as will be discussed in reference to FIG. 2 below. Pneumatic connections, and air tight connections, between blood pressure monitor 110 and pneumatic deflation valve 130, and between blood pressure cuff 120 and pneumatic deflation valve 130, are provided by a monitor hose 150 and a cuff hose 160, respectively. Monitor hose 150 and cuff hose 160 are detachably connected to valve body 170 of pneumatic deflation valve 130 at a monitor port 180 and a cuff port 190, respectively, situated on opposite sides of valve body 170, as best seen by now referring to FIG. 2.

FIG. 2, a pneumatic deflation valve 130 is shown having a rectangular valve body 170, however, valve body 170 may be oval, as depicted generally by numeral 130 in FIG. 1, or any other shape that may be aesthetically pleasing or ergonomically suitable for the intended function. Connecting monitor port 180 to cuff port 190 is a pneumatic channel 200

(alternatively air channel), which has a sealable exhaust port 210 for exhausting air from the pneumatic channel 200 to the external environment, ambient, in order to deflate blood pressure cuff 120. FIG. 2 shows two monitor ports 180, cuff ports 190, pneumatic channels 200, and sealable exhaust ports 210, however, as a general description, reference will be made in the singular, as the present invention is not restricted to a particular number of ports, channels or the like. Exhaust vent 220 in valve body 170 permits the released air from sealable exhaust port 210 to escape from pneumatic deflation valve 130. Sealable exhaust port 210 is shown transverse to pneumatic channel 200, but may be oriented in any manner suitable for providing a sealable exhaust arrangement. An actuator assembly 230, having an actuator 240, a seal carrier 250, and a link 260, is in operable communication with sealable exhaust port 210. An exhaust port seal 270 is disposed proximate sealable exhaust port 210 and is responsive to the operation of actuator assembly 230. A bias spring 280, anchored within valve body 170 at one end 282 and free at a second end 284, provides a leaf spring effect to bias actuator assembly 230, by pushing on seal carrier 250, in a first direction, thereby pressing exhaust port seal 270 against sealable exhaust port 210 to effectively prevent air leakage during operation of the automatic NIBP monitoring system 100. Bias spring 280 is shown in FIG. 2 as a leaf spring, however, any spring (e.g., a compression spring) suitable for providing a bias force on actuator assembly 230 may be used. When actuator assembly 230 is operated in the direction of arrow "F" in a second direction, sealable exhaust port 210 is unsealed, thereby permitting air in pneumatic channel 200 to escape to ambient. Exhaust port seal 270 may be securely attached to seal carrier 250 by an adhesive or other suitable means, or may be loosely captivated in a depression molded into seal carrier 250.

In an embodiment, pneumatic deflation valve 130, and more particularly actuator assembly 230, includes a push-button actuator, generally depicted by actuator 240, and is arranged for single-handed operation by an operator, thereby permitting an operator's second hand to perform a separate function. The push-button nature of actuator assembly 230 may be achieved by a piston-type actuator or a membrane-type actuator. With a piston-type actuator, actuator 240 is designed as a linear piston, and when pushed in the direction of arrow "F", actuator 240 pushes seal carrier 250 and link 260 in a linear fashion, thereby unsealing sealable exhaust port 210. With a membrane-type actuator, actuator 240 is designed as a flexible membrane (attached to valve body 170 at the perimeter and free to flex at the center), and when pushed in the direction of arrow "F", actuator 240 flexes to push seal carrier 250 and link 260 in a linear fashion, thereby unsealing sealable exhaust port 210. Upon removal of an operational force in the direction of arrow "F", bias spring 280 returns actuator assembly 230 and exhaust port seal 270 to a sealed state. For either type of actuator, valve body 170 is designed with appropriate structural detail to permit the functional action described.

The operation of pneumatic deflation valve 130 is best seen by referring to FIG. 3, which provides a flowchart of a process 300 for automatic NIBP monitoring of a patient, in combination with FIGS. 1 and 2.

At step 310, pneumatic deflation valve 130 is first actuated in order to deflate NIBP cuff 120 prior to administering the cuff to a patient. As discussed above, the actuation of pneumatic deflation valve 130 may be performed using one hand, allowing the user's other hand to squeeze the cuff. Depression of actuator 240 in the direction of arrow "F" drives link 260 and seal carrier 250 in the direction of arrow "F", which permits exhaust port seal 270 to separate from sealable exhaust port 210, thereby permitting air in pneumatic channel 200 to escape through sealable exhaust port 210 and exhaust vent 220 to ambient as blood pressure cuff 120 is squeezed. The separation of exhaust port seal 270 from sealable exhaust port 210 may occur by the force of the escaping air through sealable exhaust port 210, or may occur because exhaust port seal 270 is adhered to seal carrier 250, and therefore moves as seal carrier 250 moves. Release of an external force depressing actuator 240 in the direction of arrow "F" results in bias spring 280 returning the actuator assembly 230 and exhaust port seal 270 to a sealed state. When the blood pressure cuff 120 is appreciably deflated, it is then administered 320 to the patient.

At step 330, automatic blood pressure monitoring of the patient is performed using a NIBP cuff 120 and an automatic NIBP monitor 110, both of which are of a known type. The automatic operation of NIBP monitor 110 involves controller 140, which receives an operator signal to begin the blood pressure monitoring process, inflates the blood pressure cuff 120 to a desired pressure and then monitors the patient's blood pressure. At the conclusion of the blood pressure monitoring process, an electronic dump valve 111 internal to NIBP monitor 110 may be opened to release the pressure of blood pressure cuff 120 on the patient. However, to facilitate rapid deflation of blood pressure cuff 120, step 340 is applied.

At step 340, pneumatic deflation valve 130 is actuated, as discussed above, to rapidly deflated blood pressure cuff 120, thereby facilitating a shorter blood pressure monitoring procedure. The use of pneumatic deflation valve 130 is quicker and less expensive than typical electronic dump valves 111, and avoids the need for an operator to separate monitor or cuff hoses 150, 160 from monitor or cuff ports 180, 190 to facilitate rapid deflation of blood pressure cuff 120.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An automatic non-invasive blood pressure monitoring system, comprising:
   a blood pressure monitor having an electronic dump valve;
   a blood pressure cuff;
   a deflation valve detachably and pneumatically connected with and intermediate said blood pressure monitor and said blood pressure cuff, said deflation valve being manually operable and configured to rapidly deflate said blood pressure cuff independent of said electronic dump valve; and
   a controller for automatically controlling said blood pressure monitor;
   wherein in response to a single-handed operation of said deflation valve by an operator, said blood pressure cuff is allowed to rapidly deflate absent a need for an operator to separate said blood pressure cuff from said blood pressure monitor.

2. The automatic non-invasive blood pressure monitoring system of claim 1, further comprising:
a monitor hose pneumatically connecting said blood pressure monitor to said deflation valve; and
a cuff hose pneumatically connecting said deflation valve to said blood pressure cuff.

3. The automatic non-invasive blood pressure monitoring system of claim 2, wherein:
said monitor hose and said cuff hose are detachably connected to said deflation valve.

4. The automatic non-invasive blood pressure monitoring system of claim 3, wherein said deflation valve further comprises:
a valve body;
a monitor port at a first end of said valve body for receiving said monitor hose;
a cuff port at a second end of said valve body for receiving said cuff hose; and
an air channel intermediate said monitor port and said cuff port, wherein said air channel comprises a sealable exhaust port for exhausting air from said air channel to ambient.

5. The automatic non-invasive blood pressure monitoring system of claim 4, wherein said deflation valve further comprises:
an actuator assembly in operable communication with said sealable exhaust port;
an exhaust port seal disposed proximate said sealable exhaust port, said exhaust port seal being responsive to said actuator assembly;
a bias spring disposed within said valve body for biasing said actuator assembly in a first direction; and
said sealable exhaust port being sealed when said actuator assembly is biased in said first direction and unsealed when said actuator assembly is biased in a second direction.

6. The automatic non-invasive blood pressure monitoring system of claim 5, wherein said actuator assembly further comprises:
an actuator;
a seal carrier for supporting said exhaust port seal; and
a link disposed intermediate said actuator and said seal carrier for communicating a force between said actuator and said seal carrier.

7. The automatic non-invasive blood pressure monitoring system of claim 5, wherein said actuator assembly comprises a push-button actuator disposed within said valve body for one-hand operation of said deflation valve by an operator.

8. The automatic non-invasive blood pressure monitoring system of claim 6, wherein said bias spring is disposed proximate said seal carrier for biasing said exhaust port seal in said first direction.

9. The automatic non-invasive blood pressure monitoring system of claim 1, wherein:
said controller is disposed within said blood pressure monitor.

10. An automatic non-invasive blood pressure monitoring system, comprising:
a blood pressure monitor having a controller for automatic control thereof, a user interface, a display, and an electronic dump valve;
a blood pressure cuff; and
a deflation valve detachably and pneumatically connected with and intermediate said blood pressure monitor and said blood pressure cuff, said deflation valve being manually operable and configured to rapidly deflate said blood pressure cuff independent of said electronic dump valve, said deflation valve comprising a valve body, a monitor port at a first end of said valve body for detachably and pneumatically connecting with said blood pressure monitor, a cuff port at a second end of said valve body for detachably and pneumatically connecting with said blood pressure cuff, and an air channel intermediate said monitor port and said cuff port, said air channel comprising a sealable exhaust port for exhausting air from said air channel to ambient;
wherein in response to a single-handed operation of said deflation valve by an operator, said blood pressure cuff is allowed to rapidly deflate absent a need for an operator to separate said blood pressure cuff from said blood pressure monitor.

11. The automatic non-invasive blood pressure monitoring system of claim 10, wherein:
said monitor and cuff ports allow different sizes of said blood pressure cuff to be connected to said blood pressure monitor via said deflation valve.

* * * * *